United States Patent [19]

Denzel et al.

[11] 4,038,281
[45] July 26, 1977

[54] CERTAIN 2,7-DIHYDRO-4H-PYRAZOLO[3,4-B]PYRIDINE-5-KETONES

[75] Inventors: Theodor Denzel; Hans Hoehn, both of Regensburg, Germany

[73] Assignee: E. R. Squibb & Sons, Inc., Princeton, N.J.

[21] Appl. No.: 733,498

[22] Filed: Oct. 18, 1976

Related U.S. Application Data

[62] Division of Ser. No. 623,150, Oct. 16, 1975, abandoned.

[51] Int. Cl.$^2$ ............................................. C07D 471/04
[52] U.S. Cl. ..................... 260/296 H; 260/268 BC; 260/293.6; 260/294.8 R; 260/295 S; 260/295.5 B; 424/250; 424/256; 424/267
[58] Field of Search ................... 260/296 H, 295.5 B

[56] References Cited

U.S. PATENT DOCUMENTS

| | | | |
|---|---|---|---|
| 3,828,057 | 8/1974 | Denzel et al. | 260/296 H |
| 3,855,675 | 12/1974 | Denzel et al. | 260/296 H |
| 3,985,757 | 10/1976 | Denzel et al. | 260/294.8 C |

*Primary Examiner*—Alan L. Rotman
*Attorney, Agent, or Firm*—Lawrence S. Levinson; Merle J. Smith

[57] ABSTRACT

New derivatives of 2,7-dihydro-4H-pyrazolo[3,4-b]pyridine-5-ketones, acids and esters have the general formula

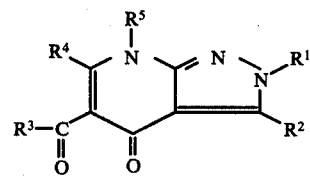

The new compounds and salts thereof are useful as central nervous depressant and antiinflammatory agents.

12 Claims, No Drawings

CERTAIN 2,7-DIHYDRO-4H-PYRAZOLO[3,4-B]PYRIDINE-5-KETONES

This is a division of application Ser. No. 623,150, filed Oct. 16, 1975, now abandoned.

SUMMARY OF THE INVENTION

This invention relates to new derivatives of 2,7-dihydro-4H-pyrazolo[3,4-b]pyridine-5-ketones and salts. These new compounds have the general formula

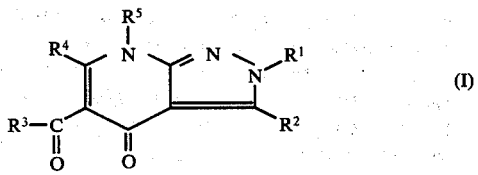

$R^1$ is lower alkyl, phenyl or phenyl-lower alkylene;
$R^2$ and $R^4$ each is hydrogen or lower alkyl;
$R^3$ is lower alkyl, phenyl, substituted phenyl, lower alkoxy or hydroxy.
$R^5$ is lower alkyl, cyclo-lower alkyl, phenyl-lower alkylene, amino-lower alkylene, di-lower alkylamino-lower alkylene, or heterocyclo-lower alkylene. (The heterocyclic is a 5 or 6-membered nitrogen heterocyclic like pyrrolidino, piperidino or piperazino.)

DETAILED DESCRIPTION OF THE INVENTION

The symbols have the following meanings in formula I and throughout this specification:

$R^1$ is lower alkyl, phenyl or phenyl-lower alkylene. The lower alkyl groups are straight or branched chain hydrocarbon groups having up to seven carbon atoms like methyl, ethyl, propyl, isopropyl, butyl, isobutyl, t-butyl, pentyl and the like. The $C_1$–$C_4$ lower alkyl groups and especially $C_1$–$C_2$ groups are preferred. The phenyl-lower alkylene groups include a phenyl group attached to a lower alkyl group such as those defined. Phenylmethyl and phenylethyl are representative and preferred.

$R^2$ and $R^4$ each is hydrogen or lower alkyl. The lower alkyl groups are the same as those defined above and the same members are preferred.

$R^3$ is hydroxy, lower alkyl, lower alkoxy, phenyl or substituted phenyl. The lower alkyl groups are of the same kind as defined with respect to $R^1$. The lower alkoxy groups include such lower alkyl groups attached to an oxygen. They include, for example, methoxy, ethoxy, propoxy, isopropoxy and the like. The $C_1$–$C_4$ lower alkoxy groups and especially $C_1$–$C_2$ groups are preferred. The substituted phenyl groups are those wherein the phenyl is simply substituted, bearing a lower alkyl, carboxy, halogen or amino group. The halogens include the four common halogens, but chlorine and bromine are preferred.

$R^5$ is lower alkyl, cyclo-lower alkyl, phenyl-lower alkylene, amino-lower alkylene, di-lower alkylamino-lower alkylene or heterocyclo-lower alkylene. Each of the lower alkyl groups has the meaning defined with respect to $R^1$ and the same groups are preferred. Each of the lower alkylene groups is a similar hydrocarbon chain, the $C_1$–$C_4$ and especially $C_1$–$C_2$ members also being preferred. The cyclo-lower alkyl groups include the $C_4$–$C_7$ cycloaliphatics cyclobutyl, cyclopentyl, cyclohexyl and cycloheptyl, the $C_5$–$C_6$ members being preferred. The amino-lower alkylene groups include, for example, aminomethyl, aminoethyl, 3-aminopropyl, 2-aminopropyl and the like. Exemplary of the di-lower alkylamino-lower alkylene groups are dimethylaminomethyl, dimethylaminoethyl, dimethylaminopropyl, diethylaminoethyl, diethylaminopropyl and the like. Groups containing up to four, but especially up to two, carbons in each of the alkyl groups are preferred.

The heterocyclo-lower alkylene group represented by $R^5$ consists of a 5- or 6-membered heterocyclic containing one or two nitrogens and the rest carbon atoms (exclusive of hydrogen) attached to a lower alkylene like those defined above. These heterocyclics are unsubstituted or substituted with lower alkyl or hydroxy-lower alkyl. Particularly they include pyrrolidine, piperidine, (lower alkyl)piperidine, piperazine, (lower alkyl)piperazine and (hydroxy-lower alkyl)piperazine. The lower alkylene groups to which the heterocyclic is attached is preferably a $C_1$–$C_4$ hydrocarbon group, particularly $C_1$–$C_2$, and especially methylene. The heterocyclics are preferably unsubstituted.

Preferred are those compounds wherein $R^1$ is lower alkyl, especially methyl; $R^2$ and $R^4$ each is hydrogen or lower alkyl, especially hydrogen. $R^3$ is lower alkoxy, hydroxy or phenyl, especially ethoxy or phenyl; $R^5$ is lower alkyl, especially methyl or ethyl, di-lower alkylamino-lower alkylene especially dimethylaminoethyl or dimethylaminopropyl, and also piperidinomethyl or piperazinomethyl.

The new compounds of formula I are formed by the following series of reactions. The symbols in the structural formulas have the same meaning as previously described.

A 5-aminopyrazole of the formula

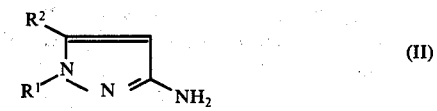

[produced analogous to the procedure described in Angew. Chem. 86, 237 (1974)] is made to react with an alkoxymethylene ester of the formula

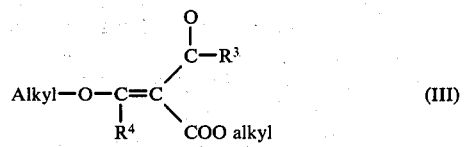

by heating at a temperature of about 120°–130° C.

The resulting compound of the formula

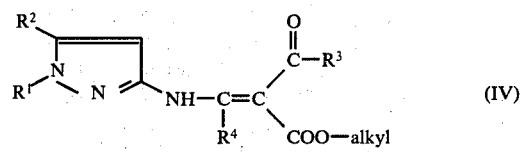

is cyclized in an inert organic solvent, such as diphenylether at about 230° to about 260°, while distilling off the alcohol formed, producing a compound of the formula

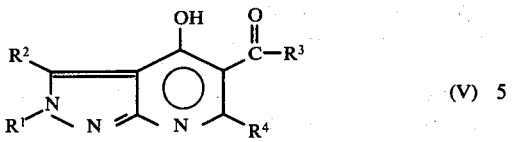

(V)

Compounds of formula I are now produced by reaction of compounds of formula V with the appropriate alkyl halide

R⁵-X (VI)

wherein R⁵ has the meaning defined above and X is halogen, especially chlorine or bromine. The reaction is effected at about 80 to 100° C. in an organic solvent like dimethylformamide, formamide or the like, in the presence of an alkali metal carbonate or hydroxide, e.g., potassium carbonate, sodium hydroxide or the like.

Basic compounds of formula I form acid addition salts which are also part of this invention, particularly the non-toxic, physiologically accepted members. The basic compounds of formula I form salts by reaction with a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a conventional means for isolating the product, e.g., by forming and precipitating the salt in a medium in which the salt is insoluble, then after separation of the salt, neutralizing with a base such as barium hydroxide or sodium hydroxide, to obtain the free base of formula I. Other salts can then be formed from the free base by reaction with one or two equivalents of the acid having the desired acid ion.

Compounds of formula I wherein R³ is hydroxy form salts with bases like alkali metal hydroxides or alkaline earth hydroxides, e.g., sodium hydroxide, potassium hydroxide, calcium hydroxide. Water soluble salts like the sodium or potassium salts are particularly useful.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance may be utilized in compositions such as tablets, capsules, solutions or suspensions containing up to about 300 mg. per unit of dosage of a compound or mixture of compounds of formula I or physiologically acceptable salt thereof. They may be compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, ointment or cream also can be used.

The new compounds of this invention are also central nervous system depressants and are useful as tranquilizers or ataractic agents for the relief of anxiety and tension states, for example, in mice, cats, rats, dogs and other mammalian species. For this purpose a compound or mixture of compounds of formula I, or non-toxic, physiologically acceptable acid addition salt thereof, is administered orally or parenterally in a conventional dosage form such as tablet, capsule, injectable or the like. A single dose, or preferably 2 to 4 divided daily doses, provided on a basis of about 1 to 50 mg. per kilogram per day, preferably about 2 to 15 mg. per kilogram per day, is appropriate. These may be conventionally formulated in an oral or parenteral dosage form by compounding about 10 to 250 mg. per unit of dosage with conventional vehicle, excipient, binder, preservative, stabilizer, flavor or the like as called for by accepted pharmaceutical practice.

The following examples are illustrative of the invention and constitute preferred embodiments. They also serve as models for the preparation of other members of the group which can be made by suitable variation of the substituent groups in the starting materials. All temperatures are in degrees celsius.

EXAMPLE 1

5-Benzoyl-2,7-dihydro-2,7-dimethyl-4H-pyrazolo[3,4-b]pyridin-4-one a.

2-[[(1-methyl-1H-pyrazol-3-yl)amino]methylene]-3-oxobenzene propanoic acid, ethyl ester 24.8 g. of ethoxymethylene-benzoylacetic acid, ethyl ester (0.1 mol.) and 9.7 g. of 3-amino-1-methylpyrazole (0.1 mol.) are heated together at 120°-130° C. for 30 minutes. After this time, the alcohol formed is distilled off in vacuo and the oily residue is crystallized with 50 ml. of ether to obtain 2-[[(1-methyl-1H-pyrazol-3-yl)-amino]methylene]-3-oxobenzenepropanoic acid, ethyl ester, yield 25 g. (84%); m.p. 65°-67°.

b.

(4-hydroxy-2-methyl-2H-pyrazolo[3,4-b]pyridin-5-yl)-phenylmethanone.

310 g. of 2-[[(1-methyl-1H-pyrazol-3-yl)amino]methylene]-3-oxobenzenepropanoic acid, ethyl ester (1.04 mol.) are heated with stirring for 15 minutes at 250° in 1 liter of diphenyl ether, while the alcohol formed is continuously distilled off. The solution is cooled and the diphenyl ether removed in vacuo. The residue is crystallized with methanol to obtain (4-hydroxy-2-methyl-2H-pyrazolo[3,4-b]-pyridin-5-yl)phenylmethanone, yield 156 g. (59.2%); m.p. 286°-290° (DMF).

c.

5-benzoyl-2,7-dihydro-2,7-dimethyl-4H-pyrazolo[3,4-b]-pyridin-4-one 25.3 g. of (4-hydroxy-2-methyl-2H-pyrazolo[3,4-b]pyridin-5-yl)phenylmethanone (0.1 mol.), 15.5 g. of methyl iodide (0.11 mol.) and 21 g. of potassium carbonate (0.15 mol.) are heated in 150 ml. of dimethylformamide with stirring at 80° for 10 hours. After this time, the inorganic precipitate is filtered off and the filtrate evaporated to dryness. The remaining 5-benzoyl-2,7-dihydro-2,7-dimethyl-4H-pyrazolo[3,4-b]pyridin-4-one is recrystallized from butanol, yield 18 g. (67%); m.p. 272°-274°.

EXAMPLE 2

5-Benzoyl-7-ethyl-2,7-dihydro-2-methyl-4H-pyrazolo[3,4-b]pyridin-4-one;

25.3 g. of (4-hydroxy-2-methyl-2H-pyrazolo[3,4-b]-pyridin-5-yl)phenylmethanone (0.1 mol.), 17.1 g. of ethyl iodide (0.11 mol.) and 5 g. of sodium hydroxide are heated together in 150 ml. of dimethylformamide for 12 hours with continuous stirring at 100°. The mixture is filtered hot, evaporated to dryness and the residue is recrystallized from butanol to obtain 5-benzoyl-7-ethyl-2,7-dihydro-2-methyl-4H-pyrazolo[3,4-b]pyridin-4-one, yield 20.3 g. (72%); m.p. 217°–218°.

EXAMPLE 3

5-Benzoyl-2,7-dihydro-2-methyl-7-(3-methylbutyl)-4H-pyrazolo[3,4-b]pyridin-4-one By substituting for the methyl iodide in the procedure of Example 1 c 1-bromo-3-methylbutane, 5-benzoyl-2,7-dihydro-2-methyl-7-(3-methylbutyl)-4H-Pyrazolo[3,4-b]pyridin-4-one is obtained, yield 69%; m.p. 231°–233° (butanol).

EXAMPLE 4

5-Benzoyl-7-[3-(dimethylamino)propyl]-2,7-dihydro-2-methyl-4H-pyrazolo[3,4-b]pyridin-4-one 5.1 g. of (4-hydroxy-2-methyl-2H-pyrazolo[3,4-b]pyridin-5-yl)phenylmethanone (0.02 mol.), 4.8 g. of dimethylaminopropyl chloride (0.04 mol.) and 5.6 g. of potassium carbonate (0.04 mol.) are heated in 50 ml. of dimethylformamide at 80° for 12 hours with stirring. The mixture is filtered hot, evaporated to dryness and the residue is recrystallized from ethyl acetate to obtain 5-benzoyl-7-[3-(dimethylamino)-propyl]-2,7-dihydro-2-methyl-4H-pyrazolo[3,4-b]pyridin-4-one, yield 4.6 g. (68%); m.p. 186°–188°.

The hydrochloride is formed by treatment with ethanolic HCl.

EXAMPLE 5

7-Ethyl-4,7-dihydro-2-methyl-4-oxo-2H-pyrazolo[3,4-b]pyridine-5-carboxylic acid, ethyl ester a.
[[(1-methyl-1H-pyrazol-3-yl)amino]methylene]-propanedioic acid, ethyl ester 194 g. of 3-amino-1-methylpyrazole (2 mol.) and 432 g. of ethoxymethylenemalonic acid, diethyl ester are stirred together for 1 hour at 100°. The alcohol formed is removed in vacuo and the residue is crystallized with ether to obtain [[(1-methyl-1H-pyrazol-3-yl)amino]methylene]-propanedioic acid, ethyl ester, yield 425 g. (80%); m.p. 60°–63°.

b.
4-hydroxy-2-methyl-2H-pyrazolo[3,4-b]pyridine-5-carboxylic acid, ethyl ester 534 g. of [[(1-methyl-1-pyrazol-3-yl)amino]methylene]propanedioic acid, ethyl ester (2 mol.) are added to about 3 liters of hot (240°) diphenyl ether (oil bath temperature 280°–290°) with stirring. The temperature of the solvent decreases to about 200°. After the temperature has again reached 220°, this temperature is maintained for 30 minutes. The alcohol formed is continuously removed by distillation. The solution is cooled to about 100° and the diphenyl ether is distilled off; (b.p. 90°–95°10.04). The oily residue is treated with 500 ml. of acetonitrile and after standing overnight, the product, 4-hydroxy-2-methyl-2H-pyrazolo[3,4-b]pyridine-5-carboxylic acid, ethyl ester, crystallizes and is purified by recrystallization from n-propyl alcohol, yield 235 g. (67%); m.p. 215°–218°.

c.
7-ethyl-4,7-dihydro-2-methyl-4-oxo-2H-pyrazolo[3,4-b]-pyridine-5-carboxylic acid, ethyl ester 22.1 g. of 4-hydroxy-2-methyl-2H-pyrazolo[3,4-b]pyridine-5-carboxylic acid, ethyl ester (0.1 mol.), 17.1 g. of ethyl iodide and 21 g. of potassium carbonate (0.15 mol.) are stirred together in 200 ml. of dimethylformamide at 80° for 12 hours. The inorganic precipitate is filtered off and the filtrate evaporated to dryness. Recrystallization of the residue with ethyl acetate yields 18.2 g. of 7-ethyl-4,7-dihydro-2-methyl-4-oxo-2H-pyrazolo[3,4-b]pyridine-5-carboxylic acid, ethyl ester, yield (73%); m.p. 170°–172°.

EXAMPLE 6

4,7-Dihydro-2,7-dimethyl-4-oxo-2H-pyrazolo[3,4-b]pyridine-5-carboxylic acid, ethyl ester By substituting methyl iodide for the ethyl iodide in the procedure of Example 5c, 4,7-dihydro-2,7-dimethyl-4-oxo-2H-pyrazolo[3,4-b]pyridine-5-carboxylic acid, ethyl ester is obtained, yield 58%; m.p. 235°–240° (butanol).

EXAMPLE 7

4,7-Dihydro-2-methyl-7-(3-methylbutyl)-4-oxo-2H-pyrazolo[3,4-b]pyridine-5-carboxylic acid, ethyl ester 22.1 g. of 4-hydroxy-2-methyl-2H-pyrazolo[3,4-b]pyridine-5-carboxylic acid, ethyl ester (0.1 mol.), 17 g. of 1-bromo-3-methylbutane and 21 g. of potassium carbonate are heated together with stirring in 100 ml. of dimethylformamide at 100° for 12 hours. The mixture is filtered hot, evaporated to dryness and the residue recrystallized from ethyl acetate to obtain 4,7-dihydro-2-methyl-7-(3-methylbutyl)-4-oxo-2H-pyrazolo[3,4-b]pyridine-5-carboxylic acid, ethyl ester, yield (63%); m.p. 105°–106°.

EXAMPLE 8

7-[3-(Dimethylamino)propyl]-4,7-dihydro-2-methyl-4-oxo-2H-pyrazolo[3,4-b]pyridine-5-carboxylic acid, ethyl ester By substituting 3-(dimethylamino)propyl chloride for the ethyl iodide in the procedure of Example 5c, 7-[3-(dimethylamino)propyl]-4,7-dihydro-2-methyl-4-oxo-2H-pyrazolo-[3,4-b]pyridine-5-carboxylic acid, ethyl ester is obtained, yield (48%); m.p. 120°–121° (ethyl acetate).

EXAMPLE 9

7-Ethyl-4,7-dihydro-2-methyl-4-oxo-2H-pyrazolo[3,4-b]pyridine-5-carboxylic acid 24.9 g. of 7-ethyl-4,7-dihydro-2-methyl-4-oxo-2H-pyrazolo[3,4-b]pyridine-5-carboxylic acid, ethyl ester (0.1 mol.) are treated with 10 g. of potassium hydroxide in 100 ml. of ethyl alcohol at reflux temperature for 12 hours with stirring. The solvent is removed in vacuo and the crystalline, residual potassium salt is dissolved in 100 ml. of water. After acidifying the solution with acetic acid, 7-ethyl-4,7-dihydro-2-methyl-4-oxo-2H-pyrazolo[3,4-b]pyridine-5-carboxylic acid crystallizes, yield 19 g. (68%); m.p. 273°–275° (DMF).

The following additional products are produced by the methods of the previous examples by appropriate substitution of the reactants:

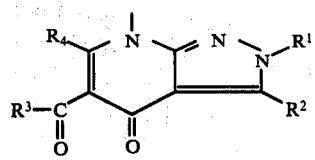
| Example | R¹ | R² | R³ | R⁴ | R⁵ |
|---|---|---|---|---|---|
| 10 | C₆H₅— | CH₃ | C₆H₅— | H | CH₃ |
| 11 | C₆H₅—CH₂CH₂— | H | CH₃ | CH₃ | CH₃ |
| 12 | C₂H₅ | H | C₂H₅ | C₂H₅ | H |
| 13 | CH₃ | H | OH | H | cyclohexyl— |
| 14 | C₆H₅— | H | OC₂H₅ | H | cyclopentyl— |
| 15 | CH₃ | H | OC₂H₅ | H | C₆H₅—CH₂— |
| 16 | CH₃ | H | OC₃H₇ | H | C₆H₅—CH₂CH₂— |
| 17 | C₂H₅ | H | 4-CH₃—C₆H₄— | H | CH₃ |
| 18 | CH₃ | CH₃ | (Cl)C₆H₄— | H | C₂H₅ |
| 19 | C₆H₅—CH₂— | H | 4-HOOC—C₆H₄— | H | CH₃ |
| 20 | CH₃ | CH₃ | 4-H₂N—C₆H₄— | CH₃ | C₂H₅ |
| 21 | CH₃ | H | OCH₃ | H | H₂N—CH₂CH₂— |
| 22 | CH₃ | CH₃ | OH | H | H₂NCH₂— |
| 23 | CH₃ | H | OH | H | (CH₃)₂NCH₂CH₂— |
| 24 | C₆H₅—CH₂— | H | CH₃ | H | (C₂H₅)₂NCH₂CH₂— |

-continued

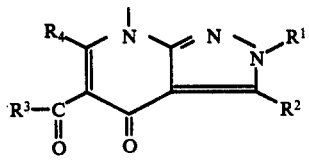

| Example | R¹ | R² | R³ | R⁴ | R⁵ |
|---|---|---|---|---|---|
| 25 | $CH_3$ | H | $OC_2H_5$ | H | azetidinyl |
| 26 | $CH_3$ | $CH_3$ | OH | H | piperidinyl |
| 27 | $C_2H_5$ | H | phenyl | H | piperazinyl (NH) |
| 28 | phenyl | H | OH | H | 4-ethylpiperidinyl |
| 29 | $CH_3$ | H | $OC_2H_5$ | $CH_3$ | 4-methylpiperazinyl |
| 30 | $CH_3$ | H | phenyl | H | 4-(2-hydroxyethyl)piperazinyl |

What is claimed is:

1. A compound of the formula

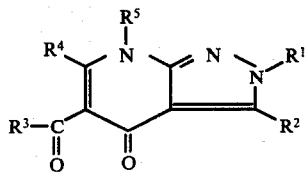

wherein
R¹ is lower alkyl, phenyl or phenyl-lower alkylene;
R² and R⁴ each is hydrogen or lower alkyl;
R³ is lower alkyl, phenyl or substituted phenyl wherein the phenyl substituent is lower alkyl, carboxy, halogen or amino;
R⁵ is lower alkyl, cyclo-lower alkyl, phenyl-lower alkylene, amino-lower alkylene or di-lower alkylamino-lower alkylene;
and physiologically acceptable acid addition salts thereof.

2. A compound as in claim 1 wherein R¹ is lower alkyl; R² and R⁴ each is hydrogen or lower alkyl; R³ is phenyl; and R⁵ is lower alkyl or di-lower alkylamino-lower alkylene.

3. A compound as in claim 1 wherein R³ is phenyl.

4. A compound as in claim 3 wherein R⁵ is lower alkyl.

5. A compound as in claim 3 wherein R⁵ is lower alkyl.

6. A compound as in claim 3 wherein R⁵ is di-lower alkylamino-lower alkylene.

7. A compound as in claim 1 wherein R² and R⁴ each is hydrogen.

8. A compound as in claim 7 wherein R¹ is methyl, R³ is phenyl and R⁵ is lower alkyl.

9. A compound as in claim 8 wherein the lower alkyl group is methyl.

10. A compound as in claim 8 wherein the lower alkyl group is ethyl.

11. A compound as in claim 7 wherein R¹ is methyl, R³ is phenyl and R⁵ is dimethylaminopropyl.

12. A compound as in claim 7 wherein R¹ is methyl, R³ is phenyl and R⁵ is 3-methylbutyl.

* * * * *